United States Patent [19]

Jolley

[11] Patent Number: 4,652,533
[45] Date of Patent: Mar. 24, 1987

[54] METHOD OF SOLID PHASE IMMUNOASSAY INCORPORATING A LUMINESCENT LABEL

[75] Inventor: Michael E. Jolley, Round Lake, Ill.

[73] Assignee: Pandex Laboratories, Inc., Mundelein, Ill.

[21] Appl. No.: 489,519

[22] Filed: Apr. 28, 1983

[51] Int. Cl.$^4$ ............... G01N 33/543; G01N 33/546; G01N 33/554; G01N 33/569

[52] U.S. Cl. .................................. 436/518; 436/519; 436/523; 436/528; 436/531; 436/533; 436/538; 436/546; 436/172; 436/807; 436/809; 435/7; 435/5; 422/52; 422/56; 422/58; 422/61

[58] Field of Search .................... 436/518-535, 436/544, 536, 538-540, 546, 807, 809, 824, 165, 172; 435/4, 7, 5, 8; 422/55-61, 52

[56] References Cited

U.S. PATENT DOCUMENTS

| | | | |
|---|---|---|---|
| Re. 29,474 | 11/1977 | Axen et al. | |
| Re. 30,562 | 3/1981 | Park | 435/296 |
| 3,992,631 | 11/1976 | Harte | 260/365 |
| 3,999,948 | 12/1976 | Deindoefer et al. | 23/230 B |
| 4,013,418 | 3/1977 | Plakas | 422/52 |
| 4,020,151 | 4/1977 | Bolz et al. | 424/12 |
| 4,025,310 | 5/1983 | Bolz et al. | 23/230 B |
| 4,039,652 | 8/1977 | Adams et al. | |
| 4,056,724 | 11/1977 | Harte | 250/328 |
| 4,090,850 | 5/1978 | Chen et al. | |
| 4,144,452 | 3/1979 | Harte | 250/302 |
| 4,163,779 | 8/1979 | Harte et al. | 424/1.1 |
| 4,201,763 | 5/1980 | Monthony et al. | 424/8 |
| 4,238,449 | 12/1980 | Deindoerfer | 422/58 |
| 4,244,940 | 1/1981 | Jeong | 424/1.1 |
| 4,271,123 | 6/1981 | Curry et al. | 422/64 |
| 4,313,929 | 2/1982 | Morita | 424/12 |
| 4,380,580 | 4/1983 | Boguslaski | 435/7 |
| 4,427,415 | 1/1984 | Cleveland | 436/57 |
| 4,459,361 | 7/1984 | Gefter | 436/523 |

OTHER PUBLICATIONS

Green, Richard L. et al, Applied Microbiology 27(3): 475-479 (1974).
Lambden, P. R. et al, Journal of Immunological Methods, 20:277-286 (1978).
Jolley, M. E. et al, Journal of Immurolional Methods, vol. 67, pp. 21-35 (1984).
Collins, M. M. et al, J. Clinical Microbiology, vol. 15(3), pp. 456-464 (1982).
Nargessi, R. D. et al, Clin. Chimica Acta, vol. 111, pp. 65-68 (1981).
Nargessi, R. D. et al, Clinica Chimica Acta, vol. 89, pp. 455-460 (1978).
Immunofiltration Catalog 1982-1983, by V & P Scientific, Inc.
Brochure: Millititer Filtration System by Millipore Corporation.
Brochure: The Sensitivity and Precision of the Microfluor System by Dynatech Laboratories, Inc.
BRL Catalog, 1981-1982 (p. 134) by Bethesda Research Laboratories, Inc.
Brochure: Minifold by Schleicher & Schuell, Inc.
Brochure: V & P by V & P Scientific, Inc.
Brochure: Protein Assays & DNA Hybridization by Millipore Corporation.
R. Curry, et al., *Clin. Chem.*, vol. 25, No. 9, pp. 1591-1595 (1979).
H. H. Handley et al., *J. of Immunological Methods*, vol. 54, pp. 291-296.
P. Cleveland, et al., *J. of Clin. Microbiol*, vol. 16, No. 4, pp. 676-685, (Oct. 1982).
P. Cleveland, et al., *J. of Clin. Microbiol*, vol. 15, No. 3, pp. 402-407, (Mar. 1982).
P. Cleveland, et al., *J. of Immunological Methods*, vol. 29, pp. 369-386 (1979).
D. Richman, *J. of Med. Virology*, vol. 9, pp. 299-305 (1982).

Primary Examiner—Charles F. Warren
Assistant Examiner—M. Moskowitz
Attorney, Agent, or Firm—Dorsey & Whitney

[57] ABSTRACT

A method is provided for solid phase immunoassay for quantitation of antigen, hapten or antibody analyte in liquid sample and alternatively for quantitation of analyte occuring on or attached to cells or other particulate material in a liquid sample. The solid phase is suspended for at least the initial reactions and is subsequently concentrated by microfiltration to a volume substantially less than the sample volume. Luminescence of substantially the entire label on the concentrated solid phase is measured.

28 Claims, No Drawings

METHOD OF SOLID PHASE IMMUNOASSAY INCORPORATING A LUMINESCENT LABEL

BACKGROUND OF THE INVENTION

1. Field of the Invention

This invention relates to a method of solid phase immunoassay incorporating a luminescent label for the quantitation of antigen, hapten or antibody analyte in a liquid sample or analyte occuring on or attached to cells or other particulate material.

2. Description of the Prior Art

A number of methods exist for the detection of substances of biological origin. One large class of methodology is the immunoassay, where antigens (or haptens) and their corresponding antibodies are used to probe the sample for each other. One very important variant of the immunoassay is the solid phase immunoassay. (Cf. Catt et al., *J. BIOCHEM*, 100: 31c (1966); Catt et al., *SCIENCE*, 158: 1570 (1967); U.S. Pat. No. 3,646,346 by Catt et al., these references and patents, and subsequently cited references and patents in the context in which they appear, are incorporated by reference thereto).

Radioactive atoms, siuch as $^{125}I$, $^{131}I$, $^{3}H$, and $^{14}C$ for example, are commonly utilized as the label in solid phase immunoassays. The resulting solid phase radioimmunoassays are quite sensitive but suffer commonly recognized disadvantages. The radioactive nature of the label subjects the assay to stringent regulatory requirements, results in a relatively short reagent shelf life and poses a waste disposal problem.

In an attempt to overcome the disadvantages of radioimmunoassays, several alternative labeling methods have been developed. Foremost among these are the enzyme immunoassays (EIA, ELISA) where an enzyme replaces the radioactive label. (cf. U.S. Pat. No. 3,551,555 by Schuurs). Enzymes commonly utilized as labels are horseradish peroxidase, alkaline phosphatase, B-galactosidase and glucose oxidase. Enzyme immunoassays have an advantage over radioimmunoassays in that the enzyme labels are very stable and special facilities and instrumentation are not required. However, enzyme immunoassays are generally slower and more tedious to perform than radioimmunoassays.

Luminescent labels have been utilized as an alternative to radioactive or enzyme labels. (cf. U.S. Pat. No. 4,201,763 by Mothony et al.; U.S. Pat. No. 3,992,631 by Harte; U.S. Pat. No. 3,999,948 by Deindoerfer et al.; A. Coons, *FLUORESCENT ANTIBODY METHODS;* J. Danielli (Editor), *GENERAL CYTOCHEMICAL METHODS* Vol. 1). Fluorescein is the most commonly used label. Although fluorescence immunoassays possess the ease of use advantage of radioimmunoassays and the reagent stability advantage of enzyme immunoassays, prior art fluorescence immunoassays lack the sensitivity of either radioimmunoassays or enzyme immunoassays. This lack of sensitivity has significance in both research and clinical applications with the result that fluorescence immunoassays have seldom been the assay of choice in these applications.

SUMMARY OF THE INVENTION

In accordance with the invention, a method of solid phase immunoassay is provided for the quantitation of antigen, hapten or antibody analyte in a liquid sample. The solid phase immunoassay incorporates a luminescent label such as a fluorescent label, a phosphorescent label or an atomic fluorescent label.

The solid phase immunoassay utilizes (i) a plurality of water insoluble particles of about 10 microns or less in size, or (ii) cells, to which an immunoreactant is attached. The analyte or an analyte containing reaction product is reacted with or in competition with or for the immunoreactant while the particles or cells are in a substantially suspended state. The particles or cells which have, or which through subsequent reaction will have, a luminescent label attached thereto are concentrated by microfiltration to a volume substantially less than the volume of the liquid sample which initially contained the analyte. The luminescence of substantialy all of the luminescent label attached to the concentrated particles or cells is measured.

Also in accordance with the invention, a method of solid phase immunoassay is provided for the quantitation of analyte occurring on or attached to cells or other particulate material contained in a liquid sample. The solid phase immunoassay incorporates a luminescent label such as those set forth above.

Analyte such as surface antigens, soluble proteins, hapten or virus, or analyte containing reaction product, is reacted with or in competition with or for an immunoreactant while the cells or particulate material on which the analyte occurs or is attached are in a substantially suspended state. The cells or particulate material which have, or which through subsequent reaction will have, a luminescent label attached thereto are concentrated by microfiltration to a volume substantially less than the volume of the liquid sample. The luminescence of substantially all of the luminescent label attached to the concentrated cells is measured.

PREFERRED EMBODIMENTS

The assay for quantitation of analyte in a liquid sample utilizes a particulate solid phase comprising cells or a plurality of water insoluble particles about 10 microns or less in size (i.e. diameter). Particles may be bacteria, mammalian cell fragments or a polymeric substrate such as, for example, polystyrene latex. Particles may be substantially transparent to a beam exciting the label and to resulting luminescence.

The speed and sensitivity of the assay are enhanced by reacting the analyte (or an analyte containing reaction product) with or in competition with or for the solid phase where the latter is suspended. The large surface area of the particulate solid phase can bring significant quantities of immunoreactants into the reaction. Substantially suspending the solid phase distributes these immunoreactants throughout the liquid medium containing the analyte (or analyte containing reaction product). This enhances rapid and complete reaction involving the analyte or analyte containing reaction product.

The assay for quantitation of analyte occurring on or attached to cells or other particulate material involves the use of the cells or particulate material as the solid phase. The cells may be, for example, bacterial or mammalian cells, while the particulate material may comprise cell fragments or a polymeric substrate. The speed and sensitivity of this assay are similarly enhanced by reacting the analyte or analyte containing reaction product with or in competition with or for an immunoreactant while the cells or particulate matter are suspended.

The solid phase of either assay may be concentrated to a volume substantially less than the volume of the liquid sample by microfiltration. This yields a two-fold advantage. First, the analyte may be concentrated prior to quantitation, thereby increasing the sensitivity of the assays by a factor substantially identical to the concentration factor. Second, the volume of the solid phase may be concentrated to a volume where a luminescence device such as, for example, a front face fluorometer may observe substantially all of the luminescent label.

A typical solid phase, for example, might comprise a 0.3% by volume suspension of 0.8 $\mu m$ particles to which an immunoreactant is attached. The solid phase contained in 20 $\mu l$ of this suspension has a surface area of 4.4 $cm^2$ and a volume of 0.06 $\mu l$. The analyte contained in 100 $\mu l$ of liquid sample will be concentrated 1,667-fold after reaction with the immunoreactant and microfiltration. The small volume of solid phase can conveniently be filtered to form a spot 1-5 mm in size (i.e. diameter). The analyte may then be reacted with a labeled immunoreactant. This will allow the fluorescence of substantially the whole solid phase to be observed by a front face fluorometer.

The assays of the present invention are useful for the quantitation of antigen, hapten or antibody analyte or analyte occurring on or attached to cells or other particulate material contained in liquid samples of body fluids such as, for example, serum, plasma, urine, saliva or non-body fluids such as, for example, cell culture media, potable water or waste water. Moreover, many biological substances of interest are present in particulate form in nature. Examples are bacterial antigens and mammalian cell surface antigens. The assay for quantitation of analyte occurring on or attached to cells or other particulate material is directly applicable to these systems. Furthermore, assays may be performed on living cells. Soluble proteins, haptens and viruses may be attached by known methods (cf. U.S. Pat. No. 4,201,763 by Monthony et al.) to microscopic latex particles, prepared by known procedures (cf. D. Blackley (Editor), *EMULSION POLYMERISATION* (Applied Science Publishers Ltd., Essex, England 1975)).

In carrying out the present assay methods, a number of alternative assay configurations are available. The following illustrates some of these possible assay configurations.

In a sandwich assay for the quantitation of antigen, hapten or antibody analyte in a liquid sample, an immunoreactant which will bind with or be bound by the analyte may be attached to the solid phase in order that the analyte be reacted with the immunoreactant. The resulting solid phase, which through subsequent reaction will have a luminescent label attached thereto, may be concentrated by microfiltration. This microfiltration may be followed by a chemical or immunological reaction of the bound analyte with a luminescent labeled material. In the alternative, the solid phase containing the analyte may be chemically or immunologically reacted with a luminescent label material prior to the concentration step. In this latter case, the solid phase, which has the luminescent label attached thereto, is concentrated by microfiltration.

As a further alternative, the analyte, for example, may be bound by a first antibody specific to the analyte, while the luminescent label is a labeled second antibody specific to the first antibody. The analyte in this case is reacted immunologically with the first antibody forming an analyte containing reaction product. The analyte containing reaction product could also be formed by a chemical reaction of some material with the analyte. The foregoing sandwich assay steps would in either case be applied to the analyte containing reaction product.

As yet a still further alternative, the analyte may be reacted with a luminescent labeled material forming an analyte containing reaction product prior to reaction with the immunoreactant which is attached to the solid phase.

In a sequential saturation assay for quantitation of antigen, hapten or antibody analyte in a liquid sample, an immunoreactant is attached to a solid phase. An excess of the immunoreactant is reacted with the analyte. A luminescent labeled material may be reacted with remaining immunoreactant sites before or after concentration by microfiltration of the solid phase. Thus, the solid phase which has, or which through subsequent reaction will have, the luminescent labeled material attached thereto is concentrated by microfiltration. Alternatively, the sequential saturation assay may be performed on an analyte containing reaction product formed either chemically or immunologically. This analyte containing product is reacted with the immunoreactant as set forth above.

In a competitive binding assay for quantitation of antigen, hapten or antibody analyte in a liquid sample, an immunoreactant is attached to a solid phase. The analyte may react in competition with the immunoreactant for a luminescent labeled material, or alternatively the analyte may react in competition with the luminescent labeled material for the immunoreactant.

In certain configurations, the immunoreactant may comprise a chemical or immunological reaction product. The latter of the two is illustrated by attaching to the solid phase a first antibody which is specific to a second antibody. The second antibody is specific to the analyte. When luminescent labeled analyte, second antibody and first antibody bound solid phase are added to a sample containing analyte, a competitive reaction of the second antibody with the analyte and labeled analyte occurs. The first and second antibody conjugate is deemed the immunoreactant.

The foregoing competitive reactions may occur prior to concentrating the solid phase by microfiltration. In this case, the solid phase which has the luminescent label attached thereto is concentrated.

It should be apparent to those skilled in the art that certain assay configurations may fall under more than one of the above discussed configurations or may be hybrids of these configurations.

In a solid phase immunoassay for quantitation of analyte occurring on or attached to cells or particulate material contained in a liquid sample, configurations similar to those set forth above allow reacting the analyte or an analyte containing reaction product with or in competition with or for an immunoreactant. In certain non-competitive reactions, the immunoreactant may itself be luminescent labeled.

The following examples will show the applicability of the present invention to the detection of monoclonal antibodies in cell culture supernatants. The examples given are characterized as sandwich assays; however, these examples serve only to demonstrate the versitility and sensitivity of the present invention and are not meant to limit its use in any way.

EXAMPLE 1

Preparation of Stock Latex Particle Suspension (I)

10 ml of 0.81 μm polystyrene latex particles (Difco, Detroit, Mich. 48232, Control 701025) were centrifuged (5000 rpm, 10 minutes) and the supernatant removed. The beads were resuspended in 20 ml of deionized water and the process repeated three times (i.e. four washes). The beads were finally suspended in 3 ml of deionized water. The final bead concentration of Latex Particle Suspension (I) was approximately 10% by volume.

EXAMPLE 2

Preparation of Lysozyme—Bead Reagent (II)

10 ml of 0.5 mg/ml of hen's egg lysozyme (Sigma, St. Louis, Mo. 63178, lot #81F-8201) in 0.01M sodium carbonate buffer (pH 9.5) was added to 1 ml of stock Latex Particle Suspension (I) and mixed thoroughly. After incubation for 3 hours at ambient temperature, the beads were centrifuged at 5000 rmp for 10 minutes and washed three times with 10 ml 0.01M sodium carbonate buffer (pH 9.5) and finally resuspended in 30 ml of the same buffer. The final concentration of Bead Reagent (II) was approximately 0.3% by volume.

EXAMPLE 3

Preparation of Fluorescein-labeled Goat anti-Mouse Ig(III)

200 μl of affinity purified goat anti-mouse Ig (Hybridoma Sciences Inc., Atlanta, Ga. 30084, cat. #701, lot #10D; 1 mg/ml in phosphate buffered saline (pH 7.4)) was added to 100 μl of 0.5M sodium carbonate buffer (ph 9.5), followed by 40 μl of fluorescein isothiocyanate isomer I (Sigma, lot #61F-5070, 1 mg/ml in phosphate buffered saline (ph 7.4)). After 1.5 hours incubation at ambient temperature, the reaction mixture was purified by passage through a Sephadex G-25 column (18×0.75 cm in phosphate buffered saline (pH 7.4)). The labeled goat anti-mouse Ig (III) was eluted from the column and collected in 1 ml total volume.

EXAMPLE 4

One Step Assay for Mouse Monoclonal Antibody to Lysozyme

A BRL #1050 MM Hybri-Dot manifold (Bethesda Research Labs., Gaithersburg, Md. 20760) was assembled with an OE66, 0.2 μm cellulose acetate filter membrane (Schleicher and Schuell, Keene, N.H. 03431), 20 μl of Bead Reagent (II) was added to each well, followed by 50 μl of sample (hybridoma growth medium, RPMI 1640 plus 15% by volume fetal bovine serum to which was diluted mouse ascites fluide from an anti-lysozyme, IgG secreting mouse hybridoma). 50 μl of a labeled goat anti-mouse Ig (III) preparation, (e.g. 5 μg/ml of labeled goat anti-mouse Ig (III) in phosphate buffered saline (pH 7.5) containing 10% by volume fetal bovine serum and 10% by volume normal goat serum) was added next. The mixture was incubated for 30 minutes at ambient temperature. Suction was then applied to the base of the manifold and, when empty, each well was washed three times with 0.4 ml water. The manifold was dismantled and the filter membrane cut into strips and laid on a piece of wet filter paper. Each dot was cut out and its front face fluorescence determined on a Hitachi Model 650-10S fluorescence spectrofluorimeter. The excitation and emission slits were opened to 20 nm and set to 0 (white light). A narrow band interference filter center wavelength 485 nm, bandwidth 10 nm was placed in the excitation beam and a wide band interference filter center wavelength 535 nm, bandwidth 20 nm in the emission beam.

Table 1 shows that ascites fluid containing mouse monoclonal anti-lysozyme may be diluted well beyond 1:64,000 and the antibody can still be detected by the assay. The assay prozones at dilutions of less than 1:4,000.

TABLE 1

Detection of Monoclonal Mouse anti-Lysozyme IgG

| Dilution of Ascites Fluid (thousandfold) | Relative Fluorescence (duplicate samples) |
| --- | --- |
| 1 | 30.5, 30.8 |
| 2 | 53.0, 56.2 |
| 4 | 74.4, 71.2 |
| 8 | 64.4, 73.1 |
| 16 | 50.0, 56.2 |
| 32 | 29.9, 31.8 |
| 64 | 20.8, 18.3 |
| ∞ | 4.1, 5.7 |

EXAMPLE 5

Two Step Assay for Mouse Monoclonal Antibody to Lysozyme

The assay was performed as in Example 4, except as follows. 50 μl of sample and 20 μl of Bead Reagent (II) were incubated for 5 minutes at ambient temperature, filtered and washed once with 0.4 ml of deionized water. 50 μl of the labeled goat anti-mouse Ig (III) preparation of Example 4 were added, followed by 15 minutes of incubation at ambient temperature. The solution was then filtered, washed three times with 0.4 ml of deionized water and the fluorescence of each spot determined.

Table 2 shows that equivalent sensitivity to the one step assay is attained in the two step assay. No prozoning was present.

TABLE 2

Two Step Assay for Detection of Mouse Monoclonal anti-Lysozyme IgG

| Dilution of Ascites Fluid (thousandfold) | Relative Fluorescence (duplicate samples) |
| --- | --- |
| 1 | 55.2, 61.2 |
| 2 | 53.5, 63.7 |
| 4 | 53.7, 69.4 |
| 8 | 48.2, 56.7 |
| 16 | 31.8, 33.7 |
| 32 | 21.0, 21.9 |
| 64 | 15.7, 16.7 |
| ∞ | 4.1, 4.9 |

EXAMPLE 6

Preparation of Latex-Human IgG Reagent (VI)

Latex particles were coated with human IgG by the method of Example 2 except that the concentration of human IgG used was 100 μg/ml. Reagent (VI) was prepared at a final particle concentration of approximately 0.3% by volume.

EXAMPLE 7

One Step Assay for Mouse Monoclonal Antibody to Human IgG

The method of Example 4 was employed using 20 μl of Reagent (VI), 50 μl of sample and 50 μl of labeled goat anti-mouse Ig (III) (2.5 μg/ml in phosphate buffered saline (ph 7.5) containing 10% by volume fetal bovine serum and 10% by volume normal goat serum). The samples were dilutions of a cell culture supernatant from an IgG producing hybridoma of antihuman IgG specificity. The incubation time was 30 minutes at ambient temperature.

Table 3 shows the results. The assay has a sensitivity of approximately 1:256 and does not prozone.

TABLE 3

One Step Assay for Mouse Monoclonal Antibody to Human IgG

| Sample Dilution | Relative Fluorescence (duplicate samples) |
| --- | --- |
| Undiluted | 64.5, 70.0 |
| 1:2 | 55.2, 55.6 |
| 1:4 | 41.0, 38.6 |
| 1:8 | 25.0, 21.8 |
| 1:16 | 15.2, 14.8 |
| 1:32 | 9.0, 8.7 |
| 1:64 | 6.2, 6.5 |
| 1:128 | 4.0, 4.0 |
| 1:256 | 3.0, 3.1 |
| 1:512 | 2.3, 2.6 |
| 1:1024 | 1.9, 2.0 |
| 1:2048 | 1.6, 1.7 |
| 1:4096 | 2.1, 1.9 |
| 1:8192 | 1.7, 1.8 |
| 1:16384 | 1.7, 1.7 |
| ∞ | 1.8, 2.0 |

EXAMPLE 8

One Step Assay for Mouse IgM Antibody to Lysozyme in Cell Culture Supernatant

The method of Example 4 was employed with 20 μl of Bead Reagent (II), 50 μl of sample and 50 μl of fluorescein-labeled, affinity purified goat anti-mouse IgM (2.5 μg/ml). The samples were dilutions of a cell culture supernatant from a hybridoma cell line secreting IgM antibody to lysozyme. The reaction mixture was incubated for 30 minutes at ambient temperature.

The results are shown in Table 4. Prozoning was again evident.

TABLE 4

One Step Assay for Mouse Igm Monoclonal Antibody to Human Lysozyme

| Sample Dilution | Relative Fluorescence (duplicate samples) |
| --- | --- |
| Undiluted | 11.9, 13.2 |
| 1:2 | 20.0, 18.2 |
| 1:4 | 19.0, 25.0 |
| 1:8 | 13.2, 15.1 |
| 1:16 | 11.0, 12.6 |
| 1:32 | 10.0, 9.0 |
| 1:64 | 7.0, 4.9 |
| 1:128 | 3.2, 3.5 |
| 1:256 | 2.9, 4.0 |
| 1:512 | 2.0, 2.3 |
| 1:1024 | 2.0, 2.4 |
| ∞ | 1.7, 1.8 |

EXAMPLE 9

Preparation of Latex-Anti-Mouse IgG Reagent (IX)

The method of Example 6 was employed. Affinity purified goat-anti-mouse IgG (Hybridoma Sciences, supra, Lot #18C) was used at 100 μg/ml in 0.01M sodium carbonate buffer (ph 9.5). An overnight incubation at ambient temperature was employed. The final concentration of Reagent (IX) was approximately 0.3% by volume.

EXAMPLE 10

Antibody Capture Assay for Mouse IgG Monoclonal Antibody Against Human IgG

The method of Example 4 was employed. 20 μl of Reagent (IX) were mixed with 50 μl of sample (dilutions in growth medium of a cell culture supernatant from a mouse hybridoma cell line producing IgG antibody to human IgG) and 50 μl of fluorescein labeled humand IgG (3 μg/ml in phosphate buffered saline (ph 7.5) containing 10% by volume fetal bovine serum and 10% by volume normal goat serum). Incubation was 30 minutes at ambient temperature. The results are shown in Table 5.

TABLE 5

Antibody Capture Assay for Mouse IgG Monoclonal Antibody to Human IgG

| Sample Dilution | Relative Fluorescence (duplicate samples) |
| --- | --- |
| Undiluted | 30.0, 30.9 |
| 1:2 | 26.2, 26.7 |
| 1:4 | 12.7, 17.4 |
| 1:8 | 10.0, 9.0 |
| 1:16 | 6.2, 7.3 |
| 1:32 | 4.9, 3.8 |
| 1:64 | 4.2, 3.2 |
| 1:128 | 2.6, 3.7 |
| 1:256 | 2.3, 3.9 |
| 1:512 | 2.4, 4.1 |
| 1:1024 | 2.9, 2.9 |
| ∞ | 2.7, 3.0 |

EXAMPLE 11

Assay for Mouse IgG

The assay was performed as in Example 4. 20 μl of Reagent (IX) were mixed with 50 μl of sample (dilutions of a cell culture supernatant from an IgG producing mouse hybridoma cell line) and 50 μl of labeled goat anti-mouse Ig (III) (2.5 μg/ml in phosphate buffered saline (ph 7.5) containing 10% by volume fetal bovine serum and 10% by volume normal goat serum). The reaction mixture was incubated for 30 minutes at ambient temperature. Table 6 shows the results.

TABLE 6

Sandwich Assay for Mouse IgG

| Sample Dilution | Relative Fluorescence (duplicate samples) |
| --- | --- |
| Undiluted | 13.0, 14.1 |
| 1:2 | 11.6, 14.3 |
| 1:4 | 12.2, 13.2 |
| 1:8 | 8.3, 9.4 |
| 1:16 | 6.3, 6.6 |
| 1:32 | 4.1, 5.4 |
| 1:64 | 3.5, 3.8 |
| 1:128 | 2.8, 3.1 |
| 1:256 | 3.4, 3.7 |
| 1:512 | 2.4, 2.6 |
| 1:1024 | 2.8, 3.3 |
| ∞ | 2.7, 3.2 |

The invention may be embodied in other specific forms than those set forth in this specification without departing from the spirit or essential characteristics thereof. Present embodiments, therefore, are to be considered in all respects as illustrative and not restrictive, the scope of the invention being indicated by the appended claims rather than by the foregoing descriptions, and all changes which come within the meaning and range of equivalency of the claims are therefore intended to be embraced therein.

I claim:

1. A luminescence solid phase immunoassay comprising:

placing within a microfiltration well (1) a sample suspected of containing an analyte, (2) a plurality of water insoluble particulates selected from the group consisting of particles having a size of not more than about 10 microns and biological cells, said particulates having attached thereto an immunoreactant specific for the analyte, and (3) a luminescent labeled material selected from the group consisting of material which selectively binds with said immunoreactant and material which selectively binds with said analyte, such that a fluid mixture is formed containing the sample, the luminescent labeled material and the particulates and such that said particulates are dispersed within said fluid mixture, resulting in a high ratio of said particulates' surface area to the fluid mixture's volume, said well containing a filter membrane, the area of the filter membrane being selected such that a sizable concentration of the particulates results upon filtration and such that a discrete measuring zone results;

incubating said fluid mixture for a time and under conditions sufficient to permit immunoreaction according to said specificity of said immunoreactant and reaction according to said binding of said luminescent labeled material;

concentrating the dispersed particulates by filtration in a manner such that a layer of substantially all the particulates is formed within the discrete measuring zone; and measuring the zone which contains the layer of concentrated particulates for luminescence.

2. A luminescence solid phase immunoassay comprising:

placing within a microfiltration well (1) a sample suspected of containing an analyte and (2) a plurality of water insoluble particulates selected from the group consisting of particles having a size of not more than about 10 microns and biological cells, said particulates having attached thereto an immunoreactant specific for the analyte, such that a fluid mixture is formed containing the sample and the particulates and such that said particulates are dispersed within said fluid mixture, resulting in a high ratio of said particulates' surface area to the fluid mixture's volume, said well containing a filter membrane, the area of the filter membrane being selected such that a sizable concentration of the particulates results upon filtration and such that a discrete measuring zone results;

incubating said fluid mixture for a time and under conditions sufficient to permit immunoreaction according to said specificity of said immunoreactant;

placing within said microfiltration well (3) a luminescent labeled material selected from the group consisting of material which selectively binds with said immunoreactant and material which selectively binds with said analyte, such that a second fluid mixture is formed containing the luminescent labeled material and the particulates and such that said particulates are dispersed within said second fluid mixture;

incubating said second fluid mixture for a time and under conditions sufficient to permit reaction according to said binding of said luminescent labeled material;

concentrating the dispersed particulates by filtration in a manner such that a layer of substantially all the particulates is formed within the discrete measuring zone; and measuring the zone which contains the layer of concentrated particulates for luminescence.

3. A luminescence solid phase immunoassay comprising:

placing within a microfiltration well (1) a sample suspected of containing an analyte and (2) a plurality of water insoluble particulates selected from the group consisting of particles having a size of not more than about 10 microns and biological cells, said particulates having attached thereto an immunoreactant specific for the analyte, such that a fluid mixture is formed containing the sample and the particulates and such that said particulates are dispersed within said fluid mixture, resulting in a high ratio of said particulates' surface area to the fluid mixture's volume, said well containing a filter membrane, the area of the filter membrane being selected such that a sizable concentration of the particulates results upon filtration and such that a discrete measuring zone results;

incubating said fluid mixture for a time and under conditions sufficient to permit immunoreaction according to said specificity of said immunoreactant;

concentrating the dispersed particulates by filtration in a manner such that a layer of substantially all the particulates is formed within the discrete measuring zone;

placing within said microfiltration well (3) a luminescent labeled material selected from the group consisting of material which selectively binds with said immunoreactant and material which selectively binds with said analyte, such that a second fluid mixture is formed containing the luminescent labeled material and the particulates;

incubating said second fluid mixture for a time and under conditions sufficient to permit reaction according to said binding of said luminescent labeled material;

filtering said second fluid mixture in a manner such that the layer of substantially all the particulates remains within or such a layer is reformed within the discrete measuring zone; and measuring the zone which contains the layer of concentrated particulates for luminescence.

4. A luminescence solid phase immunoassay comprising:

placing within a microfiltration well (1) a sample suspected of containing an analyte and (2) a luminescent labeled material which selectively binds with said analyte, such that a fluid mixture is formed containing the sample and the luminescent labeled material;

incubating said fluid mixture for a time and under conditions sufficient to permit reaction according to said binding of said luminescent labeled material;

placing within said microfiltration well (3) a plurality of water insoluble particulates selected from the group consisting of particles having a size of not more than about 10 microns and biological cells, said particulates having attached thereto an immunoreactant specific for the analyte, such that a second fluid mixture is formed containing the particulates and such that said particulates are dispersed within said fluid mixture, resulting in a high ratio of said particulates' surface area to the second fluid mixture's volume, said well containing a filter membrane, the area of the filter membrane being selected such that a sizable concentration of the particulates results upon filtration and such that a discrete measuring zone results;

incubating said fluid mixture for a time and under conditions sufficient to permit immunoreaction according to said specificity of said immunoreactant;

concentrating the dispersed particulates by filtration in a manner such that a layer of substantially all the particulates is formed within the discrete measuring zone; and measuring the zone which contains the layer of concentrated particulates for luminescence.

5. A luminescence solid phase immunoassay comprising:

placing within a microfiltration well (1) a plurality of water insoluble particulates selected from the group consisting of particles having a size of not more than about 10 microns and biological cells, said particulates having attached thereto an immunoreactant, and (2) a luminescent labeled material which selectively binds with said immunoreactant, such that a fluid mixture is formed containing the luminescent labeled material and the particulates and such that said particulates are dispersed within said fluid mixture, resulting in a high ratio of said particulates' surface area to the fluid mixture's volume, said well containing a filter membrane, the area of the filter membrane being selected such that a sizable concentration of the particulates results upon filtration and such that a discrete measuring zone results;

incubating said fluid mixture for a time and under conditions sufficient to permit reaction according to said binding of said luminescent labeled material;

placing within said microfiltration well (3) a sample suspected of containing an analyte specific for said immunoreactant, such that a second fluid mixture is formed containing the sample and the particulates and such that said particulates are dispersed within said second fluid mixture;

incubating said second fluid mixture for a time and under conditions sufficient to permit immunoreaction according to said specificity of said analyte;

concentrating the dispersed particulates by filtration in a manner such that a layer of substantially all the particulates is formed within the discrete measuring zone; and measuring the zone which contains the layer of concentrated particulates for luminescence.

6. A luminescence solid phase immunoassay comprising:

placing within a microfiltration well (1) a plurality of water insoluble particulates selected from the group consisting of particles having a size of not more than about 10 microns and biological cells, said particulates having attached thereto an immunoreactant, and (2) a luminescent labeled material which selectively binds with said immunoreactant, such that a fluid mixture is formed containing the luminescent labeled material and the particulates and such that said particulates are dispersed within said fluid mixture, resulting in a high ratio of said particulates' surface area to the fluid mixture's volume, said well containing a filter membrane, the area of the filter membrane being selected such that a sizable concentration of the particulates results upon filtration and such that a discrete measuring zone results;

incubating said fluid mixture for a time and under conditions sufficient to permit reaction according to said binding of said luminescent labeled material;

concentrating the dispersed particulates by filtration in a manner such that a layer of substantially all the particulates is formed within the discrete measuring zone;

placing within said microfiltration well (3) a sample suspected of containing an analyte specific for said immunoreactant, such that a second fluid mixture is formed containing the sample and the particulates;

incubating said second fluid mixture for a time and under conditions sufficient to permit immunoreaction according to said specificity of said analyte;

filtering said second fluid mixture in a manner such that the layer of substantially all the particulates remains within or such a layer is reformed within the discrete measuring zone; and measuring the zone which contains the layer of concentrated particulates for luminescense.

7. A luminescence solid phase immunoassay comprising:

placing within a microfiltration well (1) a sample suspected of containing an analyte, (2) a plurality of water insoluble particulates selected from the group consisting of particles having a size of not more than about 10 microns and biological cells, said particulates having attached thereto a first immunoreactant, (3) a luminescent labeled material, and (4) a second immunoreactant that is specific for said analyte and said first immunoreactant and that selectively binds with said luminescent labeled material, such that a fluid mixture is formed containing the sample, the luminescent labeled material, the second immunoreactant and the particulates and such that said particulates are dispersed within said fluid mixture, resulting in a high ratio of said particulates' surface area to the fluid mixture's volume, said well containing a filter membrane, the area of the filter membrane being selected such that a sizable concentration of the particulates results upon filtration and such that a discrete measuring zone results;

incubating said fluid mixture for a time and under conditions sufficient to permit immunoreactions accorping to said specificity of said second immunoreactant and reaction according to said binding of said second immunoreactant;

concentrating the dispersed particulates by filtration in a manner such that a layer of substantially all the particulates is formed within the discrete measuring zone; and measuring the zone which contains the layer of concentrated particulates for luminescense.

8. A luminescence solid phase immunoassay comprising:

placing within a microfiltration well (1) a sample suspected of containing an analyte, (2) a luminescent labeled material and (3) a first immunoreactant that is specific for said analyte and that selectively binds with said luminescent labeled material, such that a fluid mixture is formed containing the sample, the luminescent labeled material and the first immunoreactant;

incubating said fluid mixture for a time and under conditions sufficient to permit immunoreaction according to said specificity of said first immunoreactant and reaction according to said binding of said first immunoreactant;

placing within said microfiltration well (4) a plurality of water insoluble particulates selected from the group consisting of particles having a size of not more than about 10 microns and biological cells, said particulates having attached thereto a second immunoreactant specific for said first immunoreactant, such that a second fluid mixture is formed containing the particulates and such that said particulates are dispersed within said second fluid mixture, resulting in a high ratio of said particulates' surface area to the second fluid mixture's volume, said well containing a filter membrane, the area of the filter membrane being selected such that a sizable concentration of the particulates results upon filtration and such that a discrete measuring zone results;

incubating said second fluid mixture for a time and under conditions sufficient to permit immunoreaction according to said specificity of said second immunoreactant;

concentrating the dispersed particulates by filtration in a manner such that a layer of substantially all the particulates is formed within the discrete measuring zone; and measuring the zone which contains the layer of concentrated particulates for luminescense.

9. A luminescence solid phase immunoassay comprising:

placing within a microfiltration well (1) a sample suspected of containing an analyte and (2) a first immunoreactant that is specific for said analyte, such that a fluid mixture forms containing the sample and first immunoreactant;

incubating said fluid mixture for a time and under conditions sufficient to permit immunoreaction according to said specificity of said immunoreactant;

placing within said microfiltration well (3) a luminescent labeled material which binds with said first immunoreactant, such that a second fluid mixture is formed;

incubating said second fluid mixture for a time and under conditions sufficient to permit reaction according to said binding of said luminescent labeled material;

placing within said microfiltration well (4) a plurality of water insoluble particulates selected from the group consisting of particles having a size of not more than about 10 microns and biological cells, said particulates having attached thereto a second immunoreactant specific for said first immunoreactant, such that a third fluid mixture is formed containing the particulates and such that said particulates are dispersed within said third fluid mixture, resulting in a high ratio of said particulates' surface area to the third fluid mixture's volume, said well containing a filter membrane, the area of the filter membrane being selected such that a sizable concentration of the particulates results upon filtration and such that a discrete measuring zone results;

incubating said third fluid mixture for a time and under conditions sufficient to permit immunoreaction according to said specificity of said second immunoreactant;

concentrating the dispersed particulates by filtration in a manner such that a layer of substantially all the particulates is formed within the discrete measuring zone; and measuring the zone which contains the layer of concentrated particulates for luminescense.

10. A luminescence solid phase immunoassay comprising:

placing within a microfiltration well (1) a first immunoreactant and (2) a luminescent labeled material which binds with said first immunoreactant, such that a fluid mixture is formed containing the first immunoreactant and the luminescent labeled material;

incubating said fluid mixture for a time and under conditions sufficient to permit reaction according to said binding of said luminescent labeled material;

placing within said microfiltration well (3) a sample suspected of containing an analyte specific for said first immunoreactant, such that a second fluid mixture is formed containing the sample;

incubating said second fluid mixture for a time and under conditions sufficient to permit immunoreaction according to said specificity of said immunoreactant analyte;

placing within said microfiltration well (4) a plurality of water insoluble particulates selected from the group consisting of particles having a size of not more than about 10 microns and biological cells, said particulates having attached thereto a second immunoreactant specific for said first immunoreactant, such that a third fluid mixture is formed containing the particulates and such that said particulates are dispersed within said third fluid mixture, resulting in a high ratio of said particulates' surface area to the third fluid mixture's volume, said well containing a filter membrane, the area of the filter membrane being selected such that a sizable concentration of the particulates results upon filtration and such that a discrete measuring zone results;

incubating said third fluid mixture for a time and under conditions sufficient to permit immunoreaction according to said specificity of said second immunoreactant;

concentrating the dispersed particulates by filtration in a manner such that a layer of substantially all the particulates is formed within the discrete measuring zone; and measuring the zone which contains the layer of concentrated particulates for luminescense.

11. A luminescence solid phase immunoassay comprising:

placing within a microfiltration well a sample suspected of containing an analyte, (2) a plurality of water insoluble particulates selected from the group consisting of particles having a size of not more than about 10 microns and biological cells, said particulates having attached thereto an immunoreactant, and (3) a luminescent labeled material specific for said analyte and specific for said immunoreactant, such that a fluid mixture is formed containing the sample, the luminescent labeled material and the particulates and such that said particulates are dispersed within said fluid mixture, resulting in a high ratio of said particulates' surface area to the fluid mixture's volume, said well containing a filter membrane, the area of the filter membrane being selected such that a sizable concentration of the particulates results upon filtration and such that a discrete measuring zone results;

incubating said fluid mixture for a time and under conditions sufficient to permit immunoreaction according to said specificities of said luminescent labeled material;

concentrating the dispersed particulates by filtration in a manner such that a layer of substantially all the particulates is formed within the discrete measuring zone; and measuring the zone which contains the layer of concentrated particulates for luminescence.

12. A luminescence solid phase immunoassay comprising:

placing within a microfiltration well (1) a luminescent labeled material and (2) a plurality of water insoluble particulates selected from the group consisting of particles having a size of not more than about 10 microns and biological cells, said particulates having attached thereto an immunoreactant specific for the luminescent labeled material, such that a fluid mixture is formed containing the luminescent labeled material and the particulates and such that said particulates are dispersed within said fluid mixture, resulting in a high ratio of said particulates' surface area to the fluid mixture's volume, said well containing a filter membrane, the area of the filter membrane being selected such that a sizable concentration of the particulates results upon filtration and such that a discrete measuring zone results;

incubating said fluid mixture for a time and under conditions sufficient to permit immunoreaction according to said specificity of said immunoreactant;

placing within said microfiltration well (3) a sample suspected of containing an analyte which is specific for said luminescent labeled material, such that a second fluid mixture is formed containing the sample and the particulates and such that the particulates are dispersed within said second fluid mixture;

incubating said second fluid mixture for a time and under conditions sufficient to permit immunoreaction according to said specificity of said analyte;

concentrating the dispersed particulates by filtration in a manner such that a layer of substantially all the particulates is formed within the discrete measuring zone; and measuring the zone which contains the layer of concentrated particulates for luminescense.

13. A luminescence solid phase immunoassay comprising:

placing within a microfiltration well (1) a luminescent labeled material and (2) a plurality of water insoluble particulates selected from the group consisting of particles having a size of not more than about 10 microns and biological cells, and particulates having attached thereto an immunoreactant specific for the luminescent labeled material, such that a fluid mixture is formed containing the luminescent label material and the particulates and such that said particulates are dispersed within said fluid mixture, resulting in a high ratio of said particulates' surface area to the fluid mixture's volume, said well containing a filter membrane, the area of the filter membrane being selected such that a sizable concentration of the particulates results upon filtration and such that a discrete measuring zone results;

incubating said fluid mixture for a time and under conditions sufficient to permit immunoreaction according to said specificity of said immunoreactant;

concentrating the dispersed particulates by filtration in a manner such that a layer of substantially all the particulates is formed within the discrete measuring zone;

placing within said microfiltration well (3) a sample suspected of containing analyte which is specific for said luminescent labeled material, such that a second fluid mixture is formed containing the sample and the particulates;

incubating said second fluid mixture for a time and under conditions sufficient to permit immunoreaction according to said specificity of said analyte;

filtering said second fluid mixture in a manner such that the layer of substantially all the particulates remains within or such a layer is reformed within the discrete measuring zone; and measuring the zone which contains the layer of concentrated particulates for luminescense.

14. A luminescence solid phase immunoassay comprising:

placing within a microfiltration well (1) a sample suspected of containing an analyte and (2) a luminescent labeled material which is specific for said analyte, such that a fluid mixture is formed containing the sample and the luminescent labeled material;

incubating said fluid mixture for a time and under conditions sufficient to permit immunoreaction according to said specificity of said luminescent labeled material;

placing within said microfiltration well (3) a plurality of water insoluble particulates selected from the group consisting of particles having a size of not more than about 10 microns and biological cells, said particulates having attached thereto an immunoreactant specific for the luminescent labeled material, such that a second fluid mixture is formed containing the particulates and such that said particulates are dispersed within said fluid mixture, resulting in a high ratio of said particulates' surface area to the second fluid mixture's volume, said well containing a filter membrane, the area of the filter membrane being selected such that a sizable concentration of the particulates results upon filtration and such that a discrete measuring zone results;

incubating said second fluid mixture for a time and under conditions sufficient to permit immunoreaction according to said specificity of said immunoreactant;

concentrating the dispersed particulates by filtration in a manner such that a layer of substantially all the particulates is formed within the discrete measuring zone; and measuring the zone which contains the layer of concentrated particulates for luminescense.

15. The method of claims 1, 2, 3, 4, 5, 6, 7, 8, 9, 10, 11, 12, 13 or 14 whereinthe water insoluble particulates are particles having a size not more than about 10 microns.

16. The method of claim 15 wherein the particles having a size not more than 10 microns.

17. The method of claim 15 wherein the particles are selected from the group consisting of bacteria cell fragments, mammalian cell fragments and polymeric beads.

18. The method of claim 17 wherein the particles are polymeric beads.

19. The method of claim 18 wherein the polymeric beads comprise polystyrene latex.

20. The method of claims 1, 2, 3, 4, 5, 6, 7, 8, 9, 10, 11, 12, 13 or 14 wherein the water insoluble particulates are substantially transparent to the luminescence of the luminescent label.

21. A luminescence solid phase immunoassay comprising:

placing within a microfiltration well (1) a sample suspected of containing analyte occuring on or attached to the surface of a plurality of particulates selected from the group consisting of biological cells and microparticulate material having a size not more than that of biological cells and (2) a luminescent labeled material specific for said analyte, such that a fluid mixture is formed containing the sample and the luminescent labeled material and such that said particulates are dispersed within said fluid mixture, resulting in a high ratio of said particulates' surface area to the fluid mixture's volume, said well containing a filter membrane, the area of the filter membrane being selected such that a sizable concentration of the particulates results upon filtration and such that a discrete measuring zone results;

incubating said fluid mixture for a time and under conditions sufficient to permit immunoreaction according to said specificity of said luminescent labeled material;

concentrating the dispersed particulates by filtration in a manner such that a layer of substantially all the particulates is formed within the discrete measuring zone; and measuring the zone which contains the layer of concentrated particulates for luminescense.

22. A luminescence solid phase immunoassay comprising:

placing within a microfiltration well (1) a sample suspected of containing an analyte occurring on or attached to the surface of a plurality of particulates selected from the group consisting of biological cells and microparticulate material having a size not more than that of biological cells, (2) an immunoreactant specific for said analyte, and (3) a luminescent labeled material which binds with said immunoreactant, such that a fluid mixture is formed containing the sample, the particulates and the luminescent labeled material and such that said particulates are dispersed within said fluid mixture, resulting in a high ratio of said particulates' surface area to the fluid mixture's volume, said well containing a filter membrane, the area of the filter membrane being selected such that a sizable concentration of the particulates results upon filtration and such that a discrete measuring zone results;

incubating said fluid mixture for a time and under conditions sufficient to permit immunoreaction according to said specificity of said immunoreactant and reaction according to said binding of said luminescent labeled material;

concentrating the dispersed particulates by filtration in a manner such that a layer of substantially all the particulates is formed within the discrete measuring zone; and measuring the zone which contains the layer of concentrated particulates for luminescense.

23. A luminescense solid phase immunoassay comprising:

placing within a microfiltration well (1) a sample suspected of containing analyte occurring on or attached to the surface of a plurality of particulates selected from the group consisting of biological cells and microparticulate material having a size not more than that of biological cells and (2) an immunoreactant specific for said analyte, such that a fluid mixture is formed containing the sample and the particulates and such that said particulates are dispersed within said fluid mixture, resulting in a high ratio of said particulates' surface area to the fluid mixture's volume, said well containing a filter membrane, the area of the filter membrane being selected such that a sizable concentration of the particulates results upon filtration and such that a discrete measuring zone results;

incubating said fluid mixture for a time and under conditions sufficient to permit immunoreaction according to said specificity of said immunoreactant;

placing within said microfiltration well (3) a luminescent labeled material which binds with said immunoreactant, such that a second fluid mixture is formed containing said luminescent labeled material and said particulates and such that said particulates are dispersed within said fluid mixture;

incubating said second fluid mixture for a time and under conditions sufficient to permit reaction according to said binding of said luminescent labeled material;

concentrating the dispersed particulates by filtration in a manner such that a layer of substantially all the particulates is formed within the discrete measuring zone; and measuring the zone which contains the layer of concentrated particulates for luminescence.

24. A luminescence solid phase immunoassay comprising:

placing within a microfiltration well (1) a sample suspected of containing analyte occurring on or attached to the surface of a plurality of particulates selected from the group consisting of biological cells and microparticulate material having a size not more than that of biological cells and (2) an immunoreactant specific for said analyte, such that a fluid mixture is formed containing the sample and the particulates and such that said particulates are dispersed within said fluid mixture, resulting in a high ratio of said particulates' surface area to the fluid mixture's volume, said well containing a filter membrane, the area of the filter membrane being selected such that a sizable concentration of the particulates results upon filtration and such that a discrete measuring zone results;

incubating said fluid mixture for a time and under conditions sufficient to permit immunoreaction according to said specificity of said immunoreactant;

concentrating the dispersed particulates by filtration in a manner such that a layer of substantially all the particulates is formed within the discrete measuring zone;

placing within said microfiltration well (3) a luminescent labeled material which binds with said immunoreactant, such that a second fluid mixture is formed containing said luminescent labeled material and said particulates and such that particulates are dispersed within said fluid mixture;

incubating said second fluid mixture for a time and under conditions sufficient to permit reaction according to said binding of said luminescent labeled material;

filtering said second fluid mixture in a manner such that the layer of substantially all the particulates remains within or such a layer is reformed within the discrete measuring zone; and measuring the zone which contains the layer of concentrated particulates for luminescense.

25. The method of claims 21, 22, 23 or 24 wherein the biological cells are selected from the group consisting of bacteria cells and mammalian cells.

26. The method of claims 21, 22, 23 or 24 wherein the microparticulate material is selected from the group consisting of polymeric beads having a size of not more than about 10 microns and biological cell fragments.

27. The method of claim 26 wherein the polymeric beads have a size of not more than 10 microns.

28. The method of claims 21, 22, 23 or 24 wherein the analyte is selected from the group consisting of a biological cell surface antigen, a viral surface antigen, a bacterial surface antigen, a soluble protein, a soluble hapten and a soluble virus.

* * * * *

UNITED STATES PATENT AND TRADEMARK OFFICE
CERTIFICATE OF CORRECTION

PATENT NO. : 4,652,533

DATED : March 24, 1987

INVENTOR(S) : Michael E. Jolley

It is certified that error appears in the above-identified patent and that said Letters Patent is hereby corrected as shown below:

Abstract line five, amend the word "occuring" to read,

--occurring--

In column 1, line one of paragraph three, amend the word "siuch" to read,

--such--

In column 8, line 8, amend "humand" to read,

--human--

In column 12, line 26 of Claim 7, amend the word "accorping" to read,

--according--

UNITED STATES PATENT AND TRADEMARK OFFICE
CERTIFICATE OF CORRECTION

PATENT NO. : 4,652,533

DATED : March 24, 1987

INVENTOR(S) : Michael E. Jolley

It is certified that error appears in the above-identified patent and that said Letters Patent is hereby corrected as shown below:

In claim 21, delete lines one through eight of the claim and insert therein,

-- A luminescence solid phase immunoassay comprising: placing within a microfiltration well (1) a sample suspected of containing an analyte occurring on or attached to the surface of a plurality of particulates selected from the group consisting of polymeric beads having a size of not more than about 10 microns, biological cells and biological cell fragments, and (2) a --

In claim 22, delete lines one through eight of the claim and insert therein,

-- A luminescence solid phase immunoassay comprising: placing within a microfiltration well (1) a sample suspected of containing an analyte occurring on or attached to the surface of a plurality of particulates selected from the group consisting of polymeric beads having a size of not more than about 10 microns, biological cells and biological cell fragments, and (2) an im- --

UNITED STATES PATENT AND TRADEMARK OFFICE
CERTIFICATE OF CORRECTION

PATENT NO. : 4,652,533

DATED : March 24, 1987

INVENTOR(S) : Michael E. Jolley

It is certified that error appears in the above-identified patent and that said Letters Patent is hereby corrected as shown below:

In Claim 23, delete lines one through eight of the claim and insert therein,

—A luminescence solid phase immunoassay comprising: placing within a microfiltration well (1) a sample suspected of containing an analyte occurring on or attached to the surface of a plurality of particulates selected from the group consisting of polymeric beads having a size of not more than about 10 microns, biological cells and biological cell fragments, and (2) an—

In Claim 24, delete lines one through eight of the claim and insert therein,

—A luminescence solid phase immunoassay comprising: placing within a microfiltration well (1) a sample suspected of containing an analyte occurring on or attached to the surface of a plurality of particulates selected from the group consisting of polymeric beads having a size of not more than about 10 microns, biological cells and biological cell fragments, and (2) an—

UNITED STATES PATENT AND TRADEMARK OFFICE
CERTIFICATE OF CORRECTION

PATENT NO. : 4,652,533

DATED : March 24, 1987

INVENTOR(S) : Michael E. Jolley

It is certified that error appears in the above-identified patent and that said Letters Patent is hereby corrected as shown below:

In Claim 27, delete line one of the claim and insert therein,

--The method of claims 21, 22, 23 or 24 wherein the polymeric--

Signed and Sealed this

Ninth Day of February, 1988

Attest:

DONALD J. QUIGG

*Attesting Officer*  *Commissioner of Patents and Trademarks*